United States Patent
Shepard et al.

(10) Patent No.: US 11,708,463 B2
(45) Date of Patent: Jul. 25, 2023

(54) SPRAY DRYING PROCESS FOR LOW ASPECT RATIO PARTICLES COMPRISING POLY[(METHYL METHACRYLATE)-CO-(METHACRYLIC ACID)]

(71) Applicant: Capsugel Belgium NV, Bornem (BE)

(72) Inventors: Kimberly Shepard, Bend, OR (US); Michael Morgen, Bend, OR (US)

(73) Assignee: Capsugel Belgium NV, Bornem (BE)

( * ) Notice: Subject to any disclaimer, the term of this patent is extended or adjusted under 35 U.S.C. 154(b) by 519 days.

(21) Appl. No.: 17/044,712

(22) PCT Filed: Apr. 1, 2019

(86) PCT No.: PCT/IB2019/052676
§ 371 (c)(1),
(2) Date: Oct. 1, 2020

(87) PCT Pub. No.: WO2019/193488
PCT Pub. Date: Oct. 10, 2019

(65) Prior Publication Data
US 2021/0032413 A1    Feb. 4, 2021

Related U.S. Application Data

(60) Provisional application No. 62/653,852, filed on Apr. 6, 2018.

(51) Int. Cl.
| C08J 3/12 | (2006.01) |
| B01J 2/04 | (2006.01) |
| A61K 9/16 | (2006.01) |
| C08F 220/06 | (2006.01) |
| C08F 220/14 | (2006.01) |

(52) U.S. Cl.
CPC ............... *C08J 3/122* (2013.01); *B01J 2/04* (2013.01); *C08F 220/06* (2013.01); *C08F 220/14* (2013.01); *A61K 9/1635* (2013.01); *A61K 9/1682* (2013.01)

(58) Field of Classification Search
CPC ........ B01J 2/04; A61K 9/1682; A61K 9/1635; C08J 2/122; B01D 1/18
See application file for complete search history.

(56) References Cited

U.S. PATENT DOCUMENTS

| 6,548,555 | B1 | 4/2003 | Curatolo et al. |
| 7,887,840 | B2 | 2/2011 | Curatolo et al. |
| 8,202,540 | B1 | 6/2012 | Muller et al. |
| 8,236,328 | B2 | 8/2012 | Babcock et al. |
| 8,372,836 | B2 | 2/2013 | Ketner et al. |
| 8,431,159 | B2 | 4/2013 | Curatolo et al. |
| 8,703,196 | B2 | 4/2014 | Babcock et al. |
| 8,734,849 | B2 | 5/2014 | Lizio et al. |
| 8,796,341 | B2 | 8/2014 | Curatolo et al. |
| 8,834,929 | B2 | 9/2014 | Dobry et al. |
| 8,883,209 | B2 | 11/2014 | Babcock et al. |
| 9,211,290 | B2 | 12/2015 | Engers et al. |
| 9,283,211 | B1 | 3/2016 | Vaughn |
| 9,700,544 | B2 | 7/2017 | Vail et al. |
| 10,004,719 | B1 * | 6/2018 | Hsu ................. A61P 31/14 |
| 10,034,854 | B2 | 7/2018 | Lomuscio et al. |
| 10,143,659 | B2 | 12/2018 | Park et al. |
| 2004/0013731 | A1 * | 1/2004 | Chen ............... A61K 9/1635 514/290 |
| 2005/0031693 | A1 | 2/2005 | Babcock et al. |
| 2006/0204577 | A1 | 9/2006 | Crew et al. |
| 2008/0063708 | A1 | 3/2008 | Perlman et al. |
| 2012/0064143 | A1 | 3/2012 | Sharp et al. |
| 2013/0129826 | A1 | 5/2013 | Geibler et al. |
| 2014/0100256 | A1 | 4/2014 | Lorenz et al. |
| 2014/0171441 | A1 | 6/2014 | Babcock et al. |
| 2014/0179749 | A1 | 6/2014 | Lorenz et al. |
| 2014/0187582 | A1 | 7/2014 | Engers et al. |
| 2014/0210117 | A1 | 7/2014 | Friesen et al. |
| 2015/0064264 | A1 | 3/2015 | Appel et al. |
| 2015/0238614 | A1 | 8/2015 | Lafargue et al. |
| 2017/0014346 | A1 * | 1/2017 | Santos .................. B01J 2/04 |
| 2017/0304205 | A1 | 10/2017 | Patel |
| 2018/0071290 | A1 | 3/2018 | Suixiong et al. |
| 2018/0200201 | A1 | 7/2018 | Ciceri et al. |
| 2019/0167612 | A1 | 6/2019 | Kim et al. |

(Continued)

FOREIGN PATENT DOCUMENTS

| EP | 1643977 B1 | 10/2007 |
| EP | 1194123 B1 | 4/2012 |
| EP | 2780000 B1 | 11/2012 |
| EP | 2043610 B1 | 7/2015 |
| EP | 2365802 B1 | 8/2017 |
| EP | 2895195 B1 | 11/2017 |
| EP | 3254675 A1 | 12/2017 |
| EP | 2568964 B1 | 8/2018 |
| EP | 2939663 B1 | 9/2018 |
| JP | 5026787 B2 | 9/2012 |
| JP | 2015-529215 A | 10/2015 |
| JP | 6085307 B2 | 2/2017 |
| JP | 6170569 B2 | 7/2017 |
| JP | 6174374 B2 | 8/2017 |
| JP | 2018-516945 A | 6/2018 |

(Continued)

OTHER PUBLICATIONS

Office Action, dated Oct. 12, 2022, issued in corresponding Chinese Application No. 201980024614.4, and English language translation, 11 pages.

(Continued)

*Primary Examiner* — Mary Lynn F Theisen
(74) *Attorney, Agent, or Firm* — Klarquist Sparkman, LLP (57) ABSTRACT

Embodiments of a spray-drying process for producing low aspect ratio particles of poly[(methyl methacrylate)-co-(methacrylic acid)] (PMMAMA) are disclosed. In some examples, at least 95% of PMMAMA-containing particles made by the process have an aspect ratio <10. The particles may further include an active ingredient and/or an excipient.

14 Claims, 4 Drawing Sheets

(56) References Cited

U.S. PATENT DOCUMENTS

| | | | |
|---|---|---|---|
| 2019/0328713 A1 | 10/2019 | Chen et al. | |
| 2020/0155485 A1* | 5/2020 | Pivette | A61P 35/00 |

FOREIGN PATENT DOCUMENTS

| | | |
|---|---|---|
| WO | WO 2015/103447 A1 | 7/2015 |
| WO | WO 2015/161139 A1 | 10/2015 |
| WO | WO 2016/084105 A | 6/2016 |
| WO | WO 2016/155655 A1 | 10/2016 |
| WO | WO 2016/198576 A1 | 12/2016 |
| WO | WO 2017/032908 A1 | 3/2017 |
| WO | WO 2018/030862 A1 | 2/2018 |
| WO | WO 2018/069777 A1 | 4/2018 |
| WO | WO 2018/108128 A1 | 6/2018 |

OTHER PUBLICATIONS

Cilurzo et al., Fast-dissolving mucoadhesive microparticulate delivery system containing piroxicam, *European Journal of Pharmaceutical Sciences* 2005, 24:355-361.

Esposito et al., "Production of Eudragit Microparticles by Spray-Drying Technique: Influence of Experimental Parameters on Morphological and Dimensional Characteristics," *Pharmaceutical Development and Technology* 2000, 5(2):267-278.

Esposito et al., "Spray dried Eudragit microparticles as encapsulation devices for vitamin C," *International Journal of Pharmaceutics* 2002, 242:329-334.

International Search Report dated May 22, 2019, issued in International Application No. PCT/IB2019/052676, filed Apr. 1, 2019, 5 pages.

Nadal et al., "Spray-dried Eudragit® L100 microparticles containing ferulic acid: Formulation, in vitro cytoprotection and in vivo anti-platelet effect," *Materials Science and Engineering C* 2016, 64:318-328.

Rizi et al., "Production of pH-Responsive Microparticles by Spray Drying: Investigation of Experimental Parameter Effects on Morphological and Release Properties," *Journal of Pharmaceutical Sciences* 2011, 100:566-579.

Sunderland et al., "Application of a novel 3-fluid nozzle spray drying process for the microencapsulation of therapeutic agents using incompatible drug-polymer solutions," *Arch. Pharm. Res.* 2015, 38:566-573.

Tung et al., "Formulation and biopharmaceutical evaluation of bitter taste masking microparticles containing azithromycin loaded in dispersible tablets," *Eur. J. Pharm. Biopharm.* 2017, pp. 1-14, http://dx.doi.org/10.1016/j.epb.2017.03.017.

Vicente et al., "Fundamental analysis of particle formation in spray drying," *Powder Technology* 2013, 247:1-7.

Written Opinion dated May 22, 2019, issued in International Application No. PCT/IB2019/052676, filed Apr. 1, 2019, 7 pages.

F. Gaspar et al., "Improper Atomization," Chapter 8, section 8.1.3.2, *Amorphous Solid Dispersions Theory and Practice* 2014, ed. by Shah et al., Springer, New York, 4 pages.

\* cited by examiner

SPRAY DRYING PROCESS FOR LOW ASPECT RATIO PARTICLES COMPRISING POLY[(METHYL METHACRYLATE)-CO-(METHACRYLIC ACID)]

CROSS-REFERENCE TO RELATED APPLICATIONS

This is the U.S. National Stage of International Application No. PCT/IB2019/052676, filed Apr. 1, 2019, which was published in English under PCT Article 21(2), which in turn claims the benefit of the earlier filing date of U.S. Provisional Application No. 62/653,852, filed Apr. 6, 2018, which is incorporated by reference herein in its entirety.

FIELD

The present application relates to a spray-drying process for producing low aspect ratio particles comprising poly [(methyl methacrylate)-co-(methacrylic acid)].

BACKGROUND

Spray drying is a useful process for a number of applications. One such application is for the manufacture of solid amorphous dispersions (SADs) of active agent molecules and excipients, i.e. spray dried dispersions (SDDs). Typically these dispersions incorporate one or more active agents with one or more dispersion polymers. Such dispersions are generally known to increase the absorption of low solubility active molecules from the GI tract by increasing dissolution rate, maximizing dissolved active concentration and sustaining high active agent concentrations. Selection of appropriate dispersion polymer(s) can aid in physical and/or chemical stability and/or active agent solubilization performance of the SDD. In addition, the particle properties of such SDDs can be important not only for performance, but for manufacturability and downstream processing into, e.g. pharmaceutical solid dosage forms. Properties such as particle size, density and morphology are important for such manufacturability. When spray drying pharmaceutical powders, it is important to produce particle properties that are amenable to downstream handling and manufacturability into, e.g. pharmaceutical solid dosage forms, while at the same time having high spray drying throughput in terms of mass/time. In particular, the particles should have an aspect ratio close to one.

Spray drying poly[(methyl methacrylate)-co-(methacrylic acid)] (PMMAMA) from solutions of high polymer concentration to produce particles that have uniformly low aspect ratio has traditionally been difficult. Unlike many other dispersion polymers, PMMAMA exhibits a tendency to form long fibers or strings in the spray dried product. This has limited the use of PMMAMA for SDDs.

SUMMARY

Embodiments of a spray-drying process for producing low aspect ratio particles of poly[(methyl methacrylate)-co-(methacrylic acid)] (PMMAMA) are disclosed. In some embodiments, the process includes (a) providing a spray solution comprising an active agent and at least 5 wt % PMMAMA dissolved in a solvent, the solvent selected from methanol, ethanol, mixtures of acetone and water, mixtures of dichloromethane and ethanol, mixtures of dichloromethane and methanol, mixtures of ethanol and water, mixtures of methanol and water, mixtures of methanol and acetone, mixtures of methanol, acetone and water, mixtures of methyl ethyl ketone and water, or mixtures of tetrahydrofuran and water; (b) introducing the spray solution into an atomizer a feed rate of at least 3 kg/hr and atomizing the spray solution into a chamber to form droplets; (c) introducing a drying gas into the chamber at a flow rate of at least 72 kg/hr to dry the droplets and form a powder comprising PMMAMA containing particles, wherein a ratio of the drying gas flow rate to the spray solution feed rate is at least 5; and (d) collecting the powder from the chamber, wherein the temperature of the drying gas at an outlet of the chamber is <55° C., wherein at least 95% of the PMMAMA-containing particles have an aspect ratio <10. In certain embodiments, a ratio of the drying gas flow rate to the spray solution feed rate is from 8 to 16.

In any or all of the above embodiments, a throughput of the process may be >180 g of powder per hour. In some embodiments, at least 95% of the PMMAMA-containing particles have an aspect ratio ≤5.

In any or all of the above embodiments, the temperature of the drying gas when introduced into the chamber may be <165° C. In some embodiments, e.g., when the solvent comprises acetone, the temperature of the drying gas when introduced into the chamber may be ≤100° C.

In any or all of the above embodiments, the spray solution may comprise 5-9 wt % PMMAMA. In some embodiments, the spray solution comprises 5-7 wt % PMMAMA. In any or all of the above embodiments, the PMMAMA may have a free carboxyl group to ester group ratio within a range of from 1:0.8 to 1:2.2.

In any or all of the above embodiments, the spray solution may further comprise an excipient.

In any or all of the above embodiments, a temperature of the drying gas at an inlet of the chamber $T_{inlet}$ and a wt % of the PMMAMA in the spray solution $C_{soln}$ are selected to provide a dimensionless solvent parameter DSP <1.2

$$DSP = \frac{\left(\frac{T_{inlet} - T_{boil}}{T_{boil}}\right)}{\left(\frac{C_{skin} - C_{soln}}{C_{skin}}\right)^{0.75} \left(\frac{\Delta H_{vap}}{540}\right)^{1.25}}$$

where $T_{boil}$ is the boiling temperature of the solvent, $C_{skin}$ is a wt % concentration of the polymer in the solvent at which skinning occurs, and $\Delta H_{vap}$ is the standard enthalpy of vaporization in J/g of the solvent. In some embodiments, the $T_{inlet}$ and the $C_{soln}$ are selected to provide a dimensionless solvent parameter DSP <1.

The foregoing and other objects, features, and advantages of the invention will become more apparent from the following detailed description, which proceeds with reference to the accompanying figures.

DETAILED DESCRIPTION

This disclosure concerns embodiments of a spray drying process for making low aspect ratio particles comprising poly[(methyl methacrylate)-co-(methacrylic acid)] (PM-MAMA). In some embodiments, particles produced by the disclosed process confer a number of downstream processing advantages including, but not limited to, improved powder flow, better powder uniformity, higher process yield, and/or higher density relative to powders containing a significant fraction of high aspect ratio particles.

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The indefinite article "a" or "an" thus usually means "at least one." The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." The term "about" as used in the disclosure of numerical ranges indicates that deviation from the stated value is acceptable to the extent that the deviation is the result of measurement variability and/or yields a product of the same or similar properties. Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2). In order to facilitate review of the various embodiments of the disclosure, the following explanations of specific terms are provided:

Active: As used herein, the terms "active," "active ingredient," "active substance," "active component," "active pharmaceutical ingredient" and "active agent" have the same meaning as a component which exerts a desired physiological effect on a mammal, including but not limited to humans. Non-limiting examples of actives according to the disclosure include but are not limited to drugs, supplements, dietary supplements, such as vitamins or provitamins A, B, C, D, E, PP and their esters, carotenoids, anti-radical substances, hydroxyacids, antiseptics, molecules acting on pigmentation or inflammation, biological extracts, antioxidants, cells and cell organelles, antibiotics, macrolides, antifungals, itraconazole, ketoconazole, antiparasitics, antimalarials, adsorbents, hormones and derivatives thereof, nicotine, antihistamines, steroid and non-steroid anti-inflammatories, ibuprofen, naproxen, cortisone and derivatives thereof, anti-allergy agents, antihistamines, analgesics, local anesthetics, antivirals, antibodies and molecules acting on the immune system, cytostatics and anticancer agents, hypolipidemics, vasodilators, vasoconstrictors, inhibitors of angiotensin-converting enzyme and phosphodiesterase, fenofibrate and derivatives thereof, statins, nitrate derivatives and anti-anginals, beta-blockers, calcium inhibitors, anti-diuretics and diuretics, bronchodilators, opiates and derivatives thereof, barbiturates, benzodiazepines, molecules acting on the central nervous system, nucleic acids, peptides, anthracenic compounds, paraffin oil, polyethylene glycol, mineral salts, antispasmodics, gastric anti-secretory agents, clay gastric dressings and polyvinylpyrrolidone, aluminum salts, calcium carbonates, magnesium carbonates, starch, derivatives of benzimidazole, and combinations of the foregoing. Orally disintegrating tablets in certain embodiments of the instant disclosure may also comprise a glucuronidation inhibitor, for example, piperine.

Non-limiting examples of actives according to the present disclosure include dextromethorphan, fexofenadine, guaifenesin, loratadine, sildenafil, vardenafil, tadafil, olanzapine, risperidone, famotidine, loperamide, zolmitriptan, ondansetron, cetirizine, desloratadine, rizatriptan, piroxicam, paracetamol (acetaminophen), phloro-glucinol, nicergoline, metopimazine, dihydroergotamine, mirtazapine, clozapine, prednisolone, levodopa, carbidopa, lamotrigine, ibuprofen, oxycodone, diphenhydramine, ramosetron, tramadol, zolpidem, fluoxetine, hyoscyamine, and combinations thereof.

Placebo spray-dried particles are also within the scope of the instant disclosure.

Amorphous: Non-crystalline. Amorphous solids lack a definite crystalline structure and a well-defined melting point.

Aspect ratio: As used herein with respect to particles, the term "aspect ratio" refers to the ratio of length to width. The length is defined as the maximum straight-line distance between two points on the particle. The width is taken at the midpoint of the length, on a line perpendicular to the line which defines the length. If the particle twists or folds back over itself, then a contour length (i.e., length at maximum physical extension) measurement is used. A particle's aspect ratio may be measured by optical or electron microscopy techniques, e.g., by scanning electron microscopy whereby individual particles may be visualized at magnification and measured. ImageJ open-source software may be used to automate counting of particles with a low aspect ratio, e.g., an aspect ratio <10.

Dimensionless Solvent Parameter (DSP): The DSP is a numerical value that captures the effects of selected spray-drying parameters that influence the initial drying rate of liquid in a spray dryer—delta T, heat of vaporization, and delta C. Delta T is the different between the inlet temperature of a spray drying chamber and the boiling point of the solvent used to prepare the spray solution. The heat of vaporization is the amount of energy which the solvent must absorb to evaporate from the spray solution droplet. Delta C is the difference between the concentration of polymer in the spray solution and the concentration at which the polymer forms a solid-like skin on the spray solution.

$$DSP = \frac{\left(\frac{T_{inlet} - T_{boil}}{T_{boil}}\right)}{\left(\frac{C_{skin} - C_{soln}}{C_{skin}}\right)^{0.75}\left(\frac{\Delta H_{vap}}{540}\right)^{1.25}}$$

where $T_{inlet}$ is the inlet temperature of the drying gas, in °C.; $T_{boil}$ is the boiling point of the solvent, in °C.; $C_{skin}$ is the concentration of the polymer solution, in wt %, at which skinning occurs; $C_{soln}$ is the concentration of polymer in the spray solution, in wt %; $\Delta H_{vap}$ is the standard enthalpy of vaporization, in J/g. $\Delta H_{vap}$ is normalized by a scaling factor of 540 J/g.

Dispersion: A system in which particles are distributed throughout a continuous phase of a different composition. A solid dispersion is a system in which at least one solid component is distributed throughout another solid component. A molecular dispersion is a system in which at least one component is homogeneously or substantially homogeneously distributed on a molecular level throughout another component.

Excipient: A physiologically inert substance that is used as an additive in a pharmaceutical composition. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Examples of excipients include but are not limited to polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

PMMAMA: Poly[(methyl methacrylate)-co-(methacrylic acid)].

Powder: A composition comprising dispersed solid particles that are relatively free flowing from one another.

SAD: Solid amorphous dispersion.

SDD: Spray-dried dispersion.

Skinning: Formation of a solid polymer layer, or skin, on a surface of a polymer solution. This can be determined experimentally using a thin film prepared by blade casting at room temperature (about 22° C.). As the concentration of polymer in a solution increases, skinning occurs at the film's surface. The concentration at which skinning occurs is the "skinning concentration." For PMMAMA with a free carboxyl group to ester group ratio of about 1:1, the skinning concentration is about 15 wt % at room temperature.

String: As used herein, the term "string" refers to a particle with an aspect ratio >10.

As used herein, "w/w %" and "wt %" means by weight as a percentage of the total weight.

II. SPRAY DRYING PROCESS

This disclosure concerns embodiments of a process for spray drying particles containing poly[(methyl methacrylate)-co-(methacrylic acid)] (PMMAMA) under conditions that produce powders having a relatively high fraction of low aspect ratio particles while achieving a relatively high throughput. In some embodiments, the process produces a powder comprising PMMAMA-containing particles wherein at least 95% of the PMMAMA-containing particles (at least 95 out of 100 particles) have an aspect ratio <10 and/or the process has a throughput of at least 180 g of powder per hour.

PMMAMA is a random copolymer of methyl methacrylate and methacrylic acid. In some embodiments, the PMMAMA has a free carboxyl group to ester group ratio of from 1:0.8 to 1:2.2. In one embodiment, the free carboxyl group to ester group ratio is from 1:0.8 to 1:1.2 or from 1:0.9 to 1:1.1. In an independent embodiment, the free carboxyl group to ester group ratio is from 1:1.8 to 1:2.2 or from 1:1.9 to 1:2.1. In some embodiments, the viscosity of the PMMAMA is from 50 to 200 cps. Viscosity is measured as follows: Place 254.6 g of isopropyl alcohol and 7.9 g of water in a conical flask having a ground-glass joint. Add a quantity of PMMAMA, accurately weighed and equivalent to 37.5 g of solids on the dried basis, while stirring by means of a magnetic stirrer. Close the flask, and continue stirring until the polymer has dissolved completely. Adjust the temperature to 20+/−0.1° C. Equip a suitable rotation viscometer with a spindle having a cylinder 1.8 cm in diameter and 6.25 cm high attached to a shaft 0.32 cm in diameter, the distance from the top of the cylinder to the lower tip of the shaft being 0.75 cm, and the immersion depth being 8.15 cm (No. 1 spindle). With the spindle rotating at 30 rpm, immediately observe and record the scale reading. Convert the scale reading to centipoises by multiplying the reading by the constant for the viscometer spindle and speed employed. In certain embodiments, the PMMAMA is a commercially available polymer sold under the tradenames Eudragit® L100 having a free carboxyl group to ester group ratio of approximately 1:1 or Eudragit® S100 having a free carboxyl group to ester group ratio of approximately 1:2 (Evonik Nutrition & Care GmbH, Essen, Germany).

In any or all of the above embodiments, the process may include providing a spray solution comprising at least 5 wt % PMMAMA in a solvent, the solvent selected from methanol, ethanol, mixtures of acetone and water, mixtures of dichloromethane and ethanol, mixtures of dichloromethane and methanol, mixtures of ethanol and water, mixtures of methanol and water, mixtures of methanol and acetone, mixtures of methanol, acetone and water, mixtures of methyl ethyl ketone and water, or mixtures of tetrahydrofuran and water; introducing the spray solution into an atomizer at a feed rate of at least 3 kg/hr and atomizing the spray solution into a chamber to form droplets; introducing a drying gas into the chamber at a flow rate of at least 72 kg/hr to dry the droplets and form a powder comprising PMMAMA containing particles, wherein a ratio of the drying gas flow rate (kg/hr) to the spray solution feed rate (kg/hr) is at least 5; and collecting the powder from the chamber, wherein the temperature of the drying gas at an outlet of the chamber is <55° C., and wherein at least 95% of the PMMAMA-containing particles have an aspect ratio <10, such as an aspect ratio ≤9, ≤8, ≤7, ≤6, ≤5, ≤4 or ≤3. In some embodiments, at least 97%, at least 98%, or at least 99% of the PMMAMA-containing particles have an aspect ratio <10, such as an aspect ratio ≤9, ≤8, ≤7, ≤6, ≤5, ≤4 or ≤3. In certain embodiments at least 95%, at least 97%, at least 98%, or at least 99% of the PMMAMA-containing particles have an aspect ratio ≤5. In certain embodiments, at least 95%, at least 97%, at least 98%, or at least 99% of the PMMAMA-containing particles have an aspect ratio AR where 1≤AR<10, 1≤AR≤9, 1≤AR≤8, 1≤AR≤7, 1≤AR≤6, 1≤AR≤5, 1≤AR≤4, or 1≤AR≤3. Put another way, in any or all of the above embodiments, <5% of the PMMAMA-containing particles (based on the total number of particles) are strings, i.e., particles having an aspect ratio >10. In some embodiments, <3% or <1% of the PMMAMA-containing particles are strings. In any or all of the foregoing embodiments, providing the spray solution may further comprise dissolving PMMAMA in the solvent.

In any or all of the above embodiments, the spray solution may comprise 5-9 wt % PMMAMA. In some embodiments, the spray solution comprises 5-7 wt % PMMAMA. In certain embodiments, the PMMAMA is Eudragit® L100 polymer. In an independent embodiment, the PMMAMA is Eudragit® S100 polymer.

In any or all of the above embodiments, the process may further comprise dissolving an active agent in the solvent, thereby forming a spray solution comprising at least 5 wt % PMMAMA and the active agent. In some embodiments, the process further comprises dissolving one or more excipients in the spray solution. Advantageously, the solvent is selected such that the PMMAMA, active agent, and optional excipient(s) are soluble in the solvent. In the foregoing embodiments, the spray-dried powder includes particles comprising PMMAMA, active agent, and optionally one or more excipients. In some embodiments, the particles comprise a solid dispersion of PMMAMA, active agent, and excipient (if present). The active agent in the dried particle may be crystalline, amorphous, or any state in-between. In certain embodiments, the active agent is amorphous or substantially (i.e., at least 90 wt %) amorphous. In one embodiment, the active agent is molecularly dispersed throughout the PMMAMA. In an independent embodiment, at least some of the particles include domains of active agent, wherein the domains may comprise amorphous active agent, crystalline active agent, or a combination of amorphous and crystalline active agent.

The amount of active agent and/or non-polymer excipients in the spray solution is limited only by practical considerations for spray drying, e.g., solubility of the active/excipients, nozzle clogging, ability to sufficiently dry the spray-dried droplets, etc. In some embodiments, when an active and/or excipients is present, the solids—PMMAMA, active agent, and any optional excipients—used to prepare the spray solution comprise from >0 wt % active/excipients up to 75 wt % active/excipients, such as from >0 wt % to 70 wt %, >0 wt % to 65 wt %, >0 wt % to 60 wt %, >0 wt % to 55 wt %, or from >0 wt % to 50 wt % active/excipients, with the balance of the solids being PMMAMA.

In any or all of the above embodiments, the spray solution may have a solids content (PMMAMA plus any active and optional excipients), based on the mass of solids and solvent used to prepare the solution, of from 5 wt % to 40 wt %, with the PMMAMA content being from 5-9 wt % as previously described. Advantageously, the concentration of solids is selected to be below the skinning concentration. In one embodiment, the solids are completely dissolved in the solvent. In an independent embodiment, the solids are substantially dissolved (i.e., at least 90 wt % of the solids is dissolved). In another independent embodiment, all of the PMMAMA is dissolved and a portion of the active agent and optional excipient(s) is suspended in the spray solution. In general, the active and/or excipients have a negligible effect on solution viscosity, and the viscosity of the spray solution is primarily determined by the PMMAMA concentration. Thus, the maximum solids concentration is primarily dependent upon the PMMAMA concentration in the spray solution. In some embodiments, the total solids content is from 5-35 wt %, 5-30 wt %, 5-25 wt %, 5-20 wt %, 5-15 wt %, 5-12 wt % or 5-10 wt %, with the PMMAMA content being from 5-9 wt %. In certain embodiments, PMMAMA constitutes from 20-100 wt %, such as 25-100 wt %, 30-100 wt %, 40-100 wt %, or 50-100 wt % of the total solids used to prepare the spray solution.

In any or all of the above embodiments, the solvent may be selected from methanol, ethanol, mixtures of acetone and water, mixtures of dichloromethane (DCM) and ethanol, mixtures of DCM and methanol, mixtures of ethanol and water, mixtures of methanol and water, mixtures of methanol and acetone, mixtures of methanol, acetone and water, mixtures of methyl ethyl ketone and water, or mixtures of tetrahydrofuran and water. When the solvent mixture includes water, the water content may be up to 30 wt % water, e.g., from 1-30 wt % water, 3-30 wt % water, or 5-30 wt % water. In certain examples, the solvent mixture includes 3 wt %, 5 wt %, 10 wt %, 20 wt %, or 30 wt % water. When the solvent mixture is DCM/ethanol or DCM/methanol, the solvent mixture may include from 10-30 wt % of ethanol and/or methanol. When the solvent is a mixture of methanol and acetone, the solvent may include from 1-99 wt % methanol with the remainder of the solvent being acetone. In one embodiment, the solvent comprises methanol. In an independent embodiment, the solvent consists of methanol. In another independent embodiment, the solvent comprises a mixture of acetone and water, such as a mixture comprising 95-99 wt % acetone and 1-5 wt % water. In some examples, the solvent comprises 97 wt % acetone and 3 wt % water.

In any or all of the above embodiments, the spray solution may be introduced into the atomizer at a feed rate of at least 3 kg/hr. In some embodiments, the spray solution feed rate is at least 6 kg/hr, at least 10 kg/hr, at least 12 kg/hr, at least 15 kg/hr, or at least 18 kg/hr. The spray solution feed rate may be limited only by practical considerations such as the capacity of the spray-drying apparatus, the nozzle, etc. In some examples, the spray solution feed rate is from 3 kg/hr to 450 kg/hr, such as from 6-450 kg/hr, 10-450 kg/hr, 12-450 kg/hr, 15-450 kg/hr, or 18-450 kg/hr.

In any or all of the above embodiments, the drying gas may be introduced into the chamber at a flow rate of at least 72 kg/hr. In some embodiments, the drying gas flow rate is at least 75 kg/hr, at least 100 kg/hr, at least 125 kg/hr, or at least 150 kg/hr. In some examples, the drying gas flow rate is from 72 kg/hr to 2100 kg/hr, such as from 75-2100 kg/hr, 100-2100 kg/hr, 125-2100 kg/hr, or 150-2100 kg/hr. In any or all of the above embodiments, the atomizer may be a pressure nozzle or a two-fluid nozzle. In some embodiments, the pressure nozzle is a pressure-swirl nozzle.

In any or all of the above embodiments, the spray solution feed rate and the drying gas flow rate may be selected to provide a ratio of drying gas flow rate (kg/hr) to spray solution feed rate (kg/hr) of at least 5. In some embodiments, the ratio of drying gas flow rate to spray solution feed rate is from at least 5 to 16. In certain embodiments, the ratio of drying gas flow rate to spray solution feed rate is at least 8, such as from at least 8 to 16.

In any or all of the above embodiments, the temperature of the drying gas, when introduced into the chamber, may be <165° C. In some embodiments, the temperature of the drying gas, when introduced into the chamber, is ≤160° C., ≤150° C., ≤125° C., or ≤100° C. In some examples, the temperature of the drying gas, when introduced into the chamber, is from 70-160° C., 80-160° C., 90-160° C., 95-160° C., 95-150° C., or 95-125° C. Suitable drying gases include gases that do not react with PMMAMA, the solvent, and any other components present in the spray solution (e.g., active agents, excipients). Exemplary drying gases include, but are not limited to, nitrogen, argon, and helium. In some embodiments, the drying gas is nitrogen. In one embodiment, the solvent comprises methanol and the temperature of the drying gas, when introduced into the chamber, is <165° C. In an independent embodiment, the solvent comprises acetone and the temperature of the drying gas, when introduced into the chamber, is ≤100° C.

In any or all of the above embodiments, the temperature of the drying gas at an outlet of the chamber may be <55° C. In some embodiments, the temperature of the drying gas at the outlet is from ambient temperature to <55° C. or from ambient temperature to <50° C. In certain embodiments, the temperature of the drying gas at the outlet of the chamber is at least 50° C. less than the temperature of the drying gas when introduced into the chamber.

In any or all of the above embodiments, the process may have a throughput of >180 g of powder per hour. In some embodiments, the throughput is 200 g/hr, 250 g/hr, 300 g/hr, or even 400 g/hr. The throughput may be, for example from >180 g/hr to 180 kg/hr of powder, such as 200 g/hr to 180 kg/hr, 250 g/hr to 180 kg/hr, 300 g/hr to 180 kg/hr, or 400 g/hr to 180 kg/hr.

In any or all of the above embodiments, a temperature of the drying gas at an inlet of the chamber, $T_{inlet}$, and a wt % of PMMAMA in the spray solution, $C_{soln}$, may be selected to provide a dimensionless solvent parameter DSP, as defined herein, of <1.2. In some embodiments, $T_{inlet}$ and $C_{soln}$ are selected to provide a DSP <1, such as a DSP ≤0.95, ≤0.9, ≤0.8, ≤0.85, or ≤0.75. In general, as DSP decreases, the proportion of low aspect ratio particles in the product increases and the proportion of strings, or high aspect ratio particles, decreases. For embodiments of the disclosed solvents, $C_{skin}$ for PMMAMA is typically approximately 15 wt %. $C_{skin}$ can be determined experimentally by varying the concentration of PMMAMA in the selected solvent and determining the lowest concentration at which skinning is observed. Values for $\Delta H_{vap}$ and $T_{boil}$ may be determined from reference texts, e.g., the *CRC Handbook of Chemistry and Physics*, 98th Ed., CRC Press, 2017.

III. EXAMPLES

Example 1

Figure 1A:
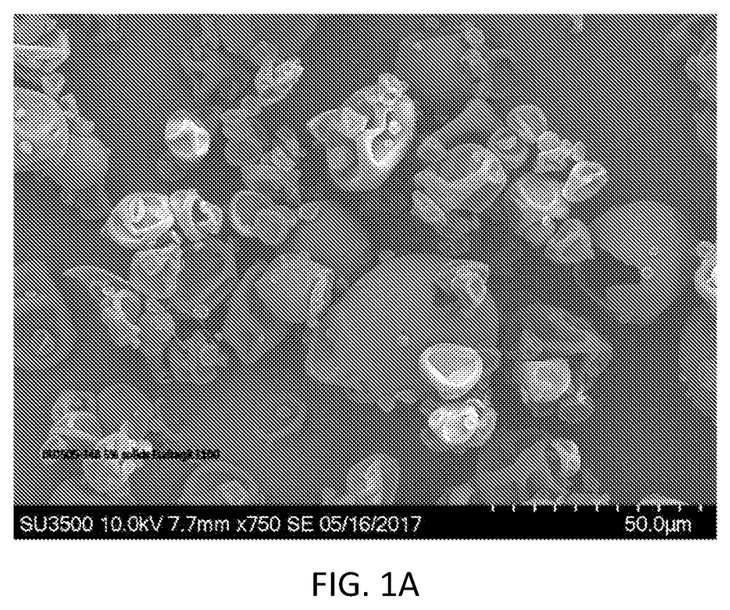
FIGS. 1A and 1B are scanning electron microscope (SEM) images of spray-dried powder prepared from solutions of 5 wt % PMMAMA (1A) and 9 wt % PMMAMA (1B) as described in Example 1.
Figure 1B:
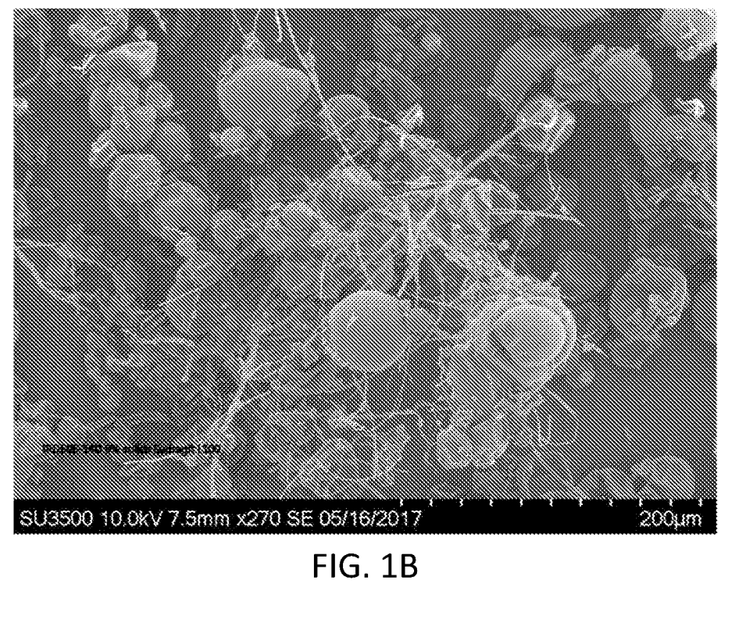

Spray solutions of 5 wt % (1A) and 9 wt % (1 B) Eudragit® L100 polymer in a solvent of 97 wt % acetone and 3 wt % water were prepared. The spray solutions were spray dried in a pre-heated spray dryer equilibrated with the spray solvent composition at a spray solution feed rate of 150 g/minute for the 5 wt % solids solution and 170 g/min for the 9 wt % solids solution, an inlet temperature of 95° C., an outlet temperature of 45° C., and a nitrogen drying gas flow rate of 1850 g/min. The solution was atomized through a pressure-swirl nozzle (Model SK80-16, Spraying Systems Co., Wheaton, Ill.) at a pressure of 400 psi. The spray-dried polymer particles were collected via a 6" cyclone separator. The dimensionless solvent parameter (DSP) for spray solution 1A was 0.84, and the DSP for spray solution 1B was 1.24. As shown in FIG. 1A, low-aspect PMMAMA-containing particles were obtained when the spray solution included 5 wt % solids, and the sample included <1% strings (particles with an aspect ratio >10) based on the total number of particles. When the solids concentration was increased to 9 wt %, a mixture of low-aspect PMMAMA-containing particles and PMMAMA strings was obtained, with the sample including >5% strings based on the total number of particles (FIG. 1B).

Example 2

Figure 2A:
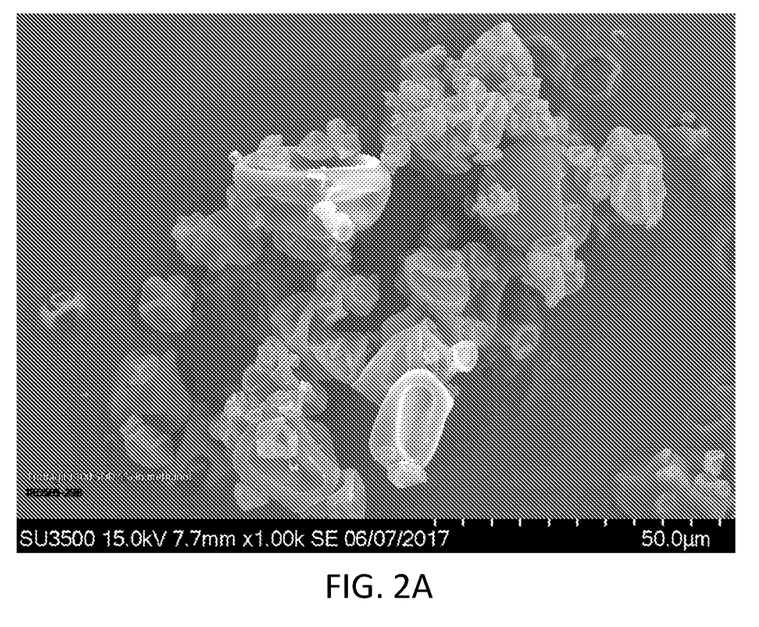
FIGS. 2A and 2B are SEM images of spray-dried powders prepared from solutions of 5 wt % (2A) and 11 wt % PMMAMA (2B) in methanol as described in Example 2.
Figure 2B:
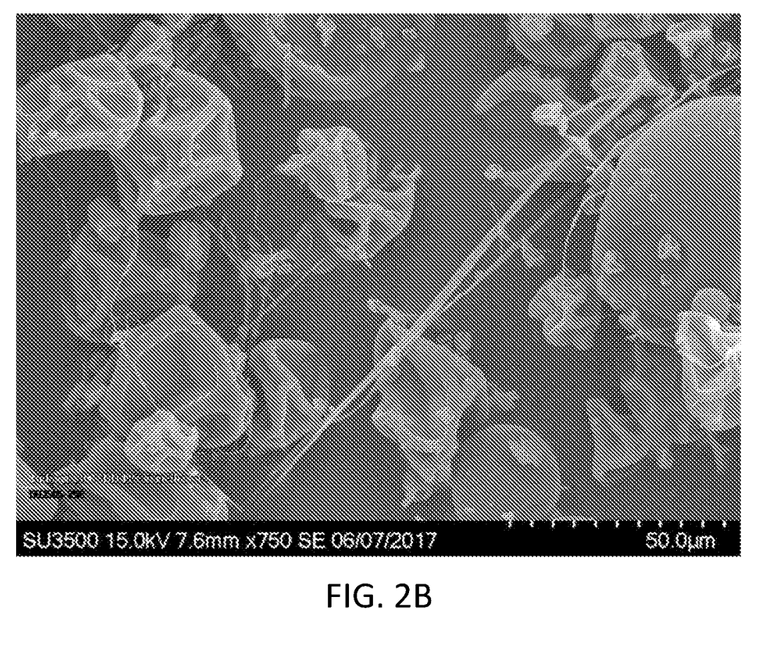

Spray solutions of 5 wt % (Example 2A) and 11 wt % (Example 2B) Eudragit® L100 polymer in methanol were prepared. The spray solutions were spray dried in a pre-heated spray dryer equilibrated with the spray solvent composition at a spray solution feed rate of 160 g/min for the 5 wt % solids solution and 205 g/min for the 11 wt % solids solution, an inlet temperature of 160° C., an outlet temperature of 45° C., and a nitrogen drying gas flow rate of 1850 g/min. The solution was atomized through a pressure-swirl nozzle (Model SK80-16, Spraying Systems Co., Wheaton, Ill.) at a pressure of 400 psi. The spray-dried polymer particles were collected via a 6" cyclone separator. The DSP for Example 2A was 0.75 and the DSP for Example 2B was 1.55. As shown in FIG. 2A, low-aspect PMMAMA-containing particles were obtained when the spray solution included 5 wt % solids. When the solids concentration was increased to 11 wt %, a mixture of low-aspect PMMAMA-containing particles and PMMAMA strings was obtained (FIG. 2B).

Example 3

Figure 3A:
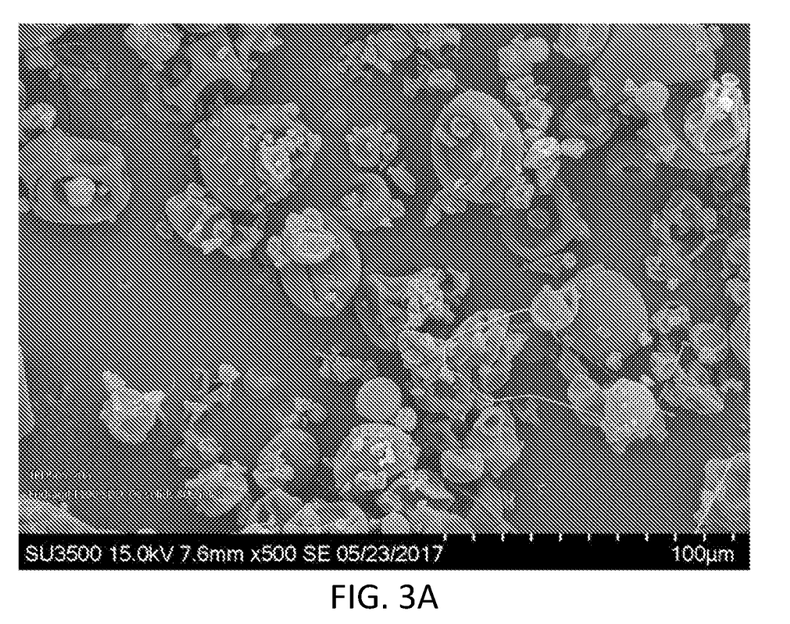
FIGS. 3A and 3B are SEM images of spray-dried powders prepared from a solution of 7 wt % PMMAMA under different process conditions as described in Example 3.
Figure 3B:
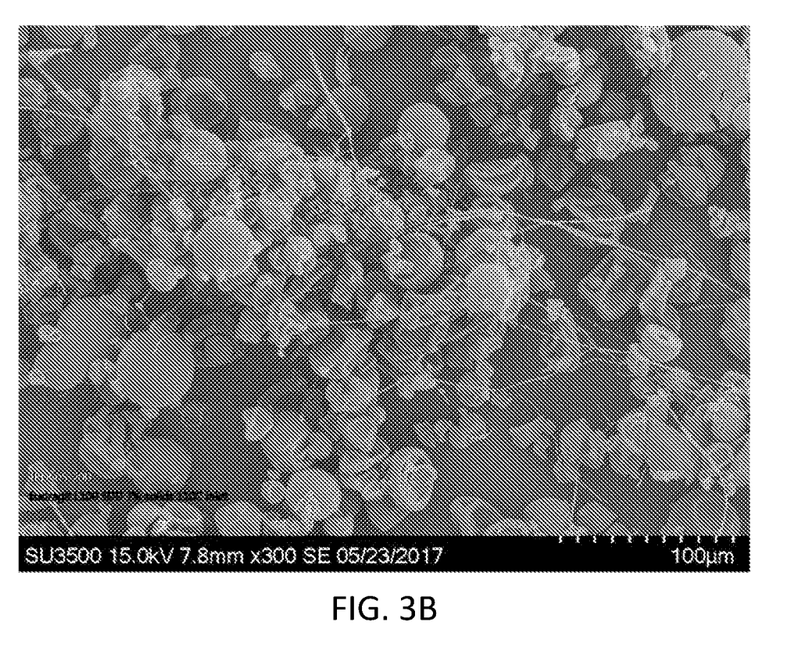

A spray solution of 7 wt % Eudragit® L100 polymer in a solvent of 97 wt % acetone and 3 wt % water was prepared. The spray solution was spray dried in a pre-heated spray dryer equilibrated with the spray solvent composition at a spray solution feed rate of 160 g/min, a nitrogen drying gas flow rate of 1850 g/min, and an inlet temperature of 80° C. with an outlet temperature of 35° C. (Example 3A), or an inlet temperature of 110° C. with an outlet temperature of 50° C. (Example 3B). The solution was atomized through a pressure-swirl nozzle (Model SK80-16, Spraying Systems Co., Wheaton, Ill.) at a pressure of 400 psi. The spray-dried polymer particles were collected via a 6" cyclone separator. The DSP for Example 3A was 0.60, and the DSP for Example 3B was 1.39. As shown in FIG. 3A, low-aspect PMMAMA-containing particles with few strings were obtained when the inlet temperature was 80° C. When the inlet temperature was increased to 110° C., an increased proportion of PMMAMA strings was obtained (FIG. 3B).

Example 4

Figure 4A:
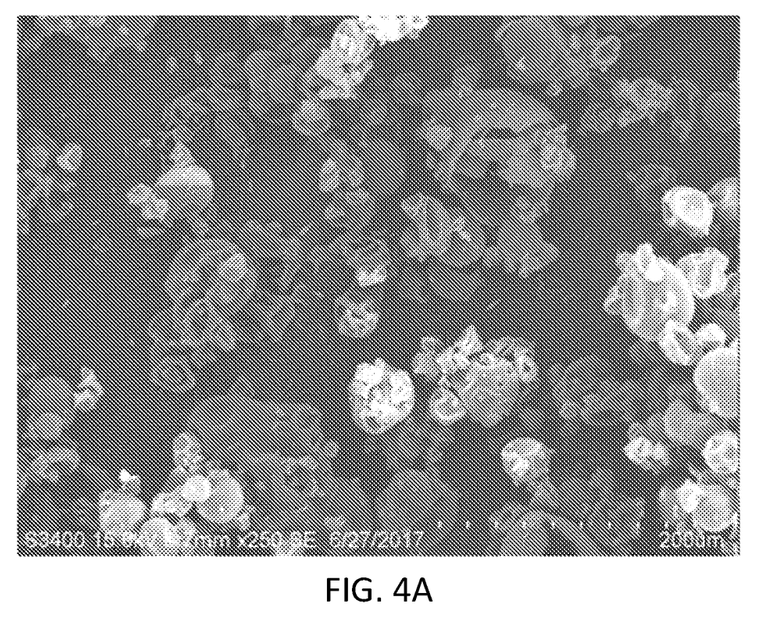
FIGS. 4A and 4B are SEM images of spray dried powders prepared from a solution of 9 wt % PMMAMA in methanol under different process conditions as described in Example 4.
Figure 4B:
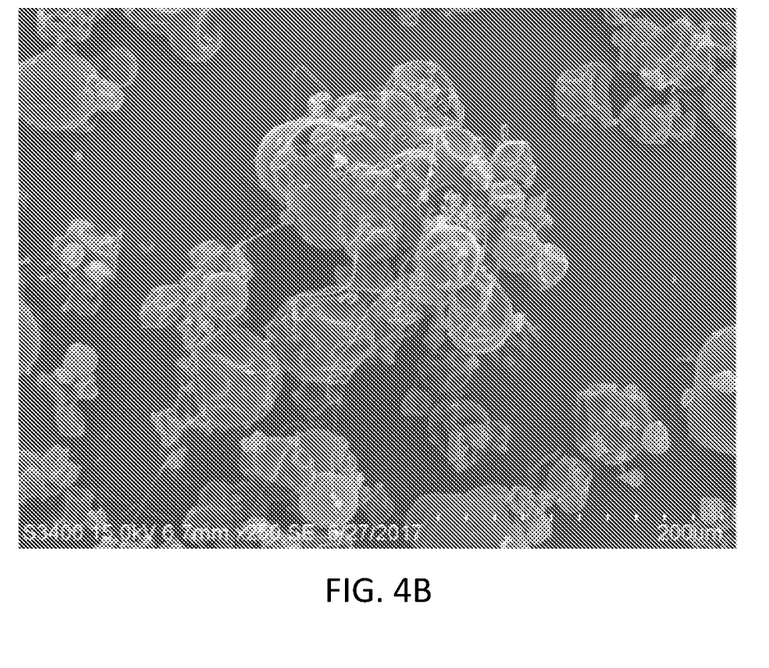

A spray solution of 9 wt % Eudragit® L100 polymer in methanol was prepared. The spray solution was spray dried in a pre-heated spray dryer equilibrated with the spray solvent composition at a spray solution feed rate of 187 g/min, an inlet temperature of 150° C. or 190° C., an outlet temperature of 35° C., and a nitrogen drying gas flow rate of 1850 g/min (with inlet temperature of 150° C., Example 4A)

or 1500 g/min (with inlet temperature of 190° C., Example 4B). The solution was atomized through a pressure-swirl nozzle (Model SK80-16, Spraying Systems Co., Wheaton, Ill.) at a pressure of 400 psi. The spray-dried polymer particles were collected via a 6" cyclone separator. The DSP for Example 4A was 0.98, and the DSP for Example 4B was 1.39. As shown in FIG. 4A, low-aspect PMMAMA-containing particles were obtained when the inlet temperature was 150° C. and the drying gas flow rate was 1850 g/min. When the inlet temperature was increased to 190° C. and the drying gas flow rate was reduced to 1500 g/min., a mixture of low-aspect PMMAMA-containing particles and PMMAMA strings was obtained (FIG. 4B).

Example 5

A spray solution comprising at least 5 wt % PMMAMA, such as 5-9 wt % PMMAMA, and an active in a solvent is prepared, the solvent selected from methanol, ethanol, mixtures of acetone and water, mixtures of dichloromethane and ethanol, mixtures of dichloromethane and methanol, mixtures of ethanol and water, mixtures of methanol and water, mixtures of methanol and acetone, mixtures of methanol, acetone and water, mixtures of methyl ethyl ketone and water, or mixtures of tetrahydrofuran and water. The spray solution may further include one or more excipients. The spray solution is introduced into an atomizer at a feed rate of at least 3 kg/hr, such as 3-450 kg/hr, and atomized into a chamber to form droplets. At the same time, a drying gas (e.g., nitrogen) is introduced into the chamber at a flow rate of at least 72 kg/hr, such as 72-2100 kg/hr, to dry the droplets and form a powder comprising particles of PMMAMA and the active. In some instances, the drying gas, when introduced into the chamber, has a temperature <165° C. The drying gas flow rate and spray solution feed rate are selected such that a ratio of the drying gas flow rate to the spray solution feed is at least 5, e.g., within a range of from 5 to 16, or from 8 to 16. The powder is collected from the chamber, e.g., via a cyclone separator. The temperature of the drying gas at the chamber outlet is less than 50° C. At least 95% of the particles have an aspect ratio <10.

Example 6

A spray solution comprising at least 5 wt % PMMAMA and an active in a solvent is prepared, the solvent selected from methanol, ethanol, mixtures of acetone and water, mixtures of dichloromethane and ethanol, mixtures of dichloromethane and methanol, mixtures of ethanol and water, mixtures of methanol and water, mixtures of methanol and acetone, mixtures of methanol, acetone and water, mixtures of methyl ethyl ketone and water, or mixtures of tetrahydrofuran and water. The spray solution may further include one or more excipients. The spray solution is introduced into an atomizer at a feed rate of at least 3 kg/hr and atomized into a chamber to form droplets. At the same time, a drying gas (e.g., nitrogen) is introduced into the chamber at a flow rate of at least 72 kg/hr to dry the droplets and form a powder comprising particles of PMMAMA and the active. The powder is collected from the chamber. The drying gas temperature at the outlet of the chamber is typically <55° C. The temperature of the drying gas at the inlet and the PMMAMA concentration in the spray solution are selected to provide a dimensionless solvent parameter, as defined herein, of <1. When the PMMAMA is provided by Eudragit® L100 polymer, the value of $C_{skin}$ is about 15 wt % in solvents prepared by methanol, acetone, and mixtures of methanol and/or acetone with water. At least 95% of the particles have an aspect ratio <10.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A process for spray drying poly[(methyl methacrylate)-co-(methacrylic acid)] (PMMAMA) comprising:

(a) providing a spray solution comprising an active agent and at least 5 wt % PMMAMA dissolved in a solvent, the solvent selected from methanol, ethanol, mixtures of acetone and water, mixtures of dichloromethane and ethanol, mixtures of dichloromethane and methanol, mixtures of ethanol and water, mixtures of methanol and water, mixtures of methanol and acetone, mixtures of methanol, acetone and water, mixtures of methyl ethyl ketone and water, or mixtures of tetrahydrofuran and water;

(b) introducing the spray solution into an atomizer a feed rate of at least 3 kg/hr and atomizing the spray solution into a chamber to form droplets;

(c) introducing a drying gas into the chamber at a flow rate of at least 72 kg/hr to dry the droplets and form a powder comprising PMMAMA containing particles, wherein a ratio of the drying gas flow rate to the spray solution feed rate is at least 5; and (d) collecting the powder from the chamber, wherein the temperature of the drying gas at an outlet of the chamber is <55° C., wherein at least 95% of the PMMAMA-containing particles have an aspect ratio <10.

2. The process of claim 1 wherein a temperature of the drying gas at an inlet of the chamber $T_{inlet}$ and a wt % of the PMMAMA in the spray solution $C_{soln}$ are selected to provide a dimensionless solvent parameter DSP <1.2

$$DSP = \frac{\left(\frac{T_{inlet} - T_{boil}}{T_{boil}}\right)}{\left(\frac{C_{skin} - C_{soln}}{C_{skin}}\right)^{0.75}\left(\frac{\Delta H_{vap}}{540}\right)^{1.25}}$$

where $T_{boil}$ is the boiling temperature of the solvent, $C_{soln}$ is a wt % concentration of the polymer in the solvent at which skinning occurs, and $\Delta H_{vap}$ is the standard enthalpy of vaporization in J/g of the solvent.

3. The process of claim 2 wherein the temperature of the drying gas at an inlet of the chamber $T_{inlet}$ and the wt % of the PMMAMA in the spray solution $C_{soln}$ are selected to provide a dimensionless solvent parameter DSP <1.

4. The process of claim 1 wherein the ratio of the drying gas flow rate to the spray solution feed rate is from 5 to 16.

5. The process of claim 1 wherein the solvent comprises methanol.

6. The process of claim 1 wherein the temperature of the drying gas, when introduced into the chamber, is <165° C.

7. The process of claim 1 wherein the spray solution comprises 5-9 wt % PMMAMA.

8. The process of claim 1 wherein the solvent comprises acetone.

9. The process of claim 8 wherein the temperature of the drying gas, when introduced into the chamber, is ≤100° C.

10. The process of claim 1 wherein the spray solution comprises 5-7 wt % PMMAMA.

11. The process of claim 1 wherein the PMMAMA has a free carboxyl group to ester group ratio of from 1:0.8 to 1:2.2.

12. The process of claim 1 wherein at least 95% of the PMMAMA-containing particles have an aspect ratio ≤5.

13. The process of claim 1 wherein a throughput of the process is >180 g of powder per hour.

14. The process of claim 1 wherein the spray solution further comprises an excipient.

\* \* \* \* \*